(12) United States Patent
Huang et al.

(10) Patent No.: US 9,446,053 B2
(45) Date of Patent: Sep. 20, 2016

(54) METHOD FOR ENHANCING THE SECRETION OF GLP-1 USING BITTER COMPOUNDS

(71) Applicant: National Taiwan University, Taipei (TW)

(72) Inventors: Ching-jang Huang, Taipei (TW); Yi-ping Pai, Taipei (TW); Ting-ni Huang, Taipei (TW)

(73) Assignee: National Taiwan University, Taipei (TW)

( * ) Notice: Subject to any disclaimer, the term of this patent is extended or adjusted under 35 U.S.C. 154(b) by 163 days.

(21) Appl. No.: 13/855,108

(22) Filed: Apr. 2, 2013

(65) Prior Publication Data
US 2014/0228332 A1   Aug. 14, 2014

(30) Foreign Application Priority Data
Feb. 8, 2013   (TW) .............................. 102105095 A

(51) Int. Cl.
| | | |
|---|---|---|
| *A61K 31/58* | (2006.01) | |
| *A61K 31/26* | (2006.01) | |
| *A61K 31/575* | (2006.01) | |

(52) U.S. Cl.
CPC ............... *A61K 31/58* (2013.01); *A61K 31/26* (2013.01); *A61K 31/575* (2013.01)

(58) Field of Classification Search
CPC ..... A61K 31/26; A61K 31/575; A61K 31/58
See application file for complete search history.

(56) References Cited

U.S. PATENT DOCUMENTS

2012/0252772 A1   10/2012   Huang et al.

FOREIGN PATENT DOCUMENTS

EP   1961418 A1 *   8/2008

OTHER PUBLICATIONS

Huang et al., "Role of GLP-1 in the Hypoglycemic Effects of Wild Bitter Gourd," Evidence-Based Complementary and Alternative Medicine, 2013, vol. 2013, Article ID 625892, 13 pages, http://dx.doi.org/10.1155/2013/625892.

Nguyen et al., Cucurbitane-type triterpene glycosides from the fruits of Momordica charantia, Magnetic Resonance in Chemistry, 2010, pp. 392-396, 48.

Murakami et al., Medicinal Foodstuffs. XXI Structures of New Cucurbitane-Type Triterpene Glycosides, Goyaglycosides-a, -b, -c, -d, -e, -f, -g, and -h, and New Oleanane-Type Triterpene Saponins, Goyasaponins I, II, and III, from the Fresh Fruit of Japanese Momordica charantia L, Chem. Pharm. Bull., 2001, pp. 54-63, vol. 49(1).

* cited by examiner

*Primary Examiner* — Sreeni Padmanabhan
*Assistant Examiner* — Jody Karol
(74) *Attorney, Agent, or Firm* — WPAT, P.C., Intellectual Property Attorneys; Anthony King

(57) ABSTRACT

The present invention provides a method for enhancing the secretion of GLP-1 of the intestinal endocrine L-cells using a bitter compound, wherein the bitter compound is a cucurbitane-triterpenoid or allyl isothiocyanate. The bitter compound can regulate the secretion of GLP-1, thus is potentially reliable for the development of medicament or healthy victual.

2 Claims, 5 Drawing Sheets

METHOD FOR ENHANCING THE SECRETION OF GLP-1 USING BITTER COMPOUNDS

CROSS-REFERENCES TO RELATED APPLICATIONS

This application claims priority to Taiwan Patent Application No. 102105095 filed on 8 Feb. 2013. All disclosure of which is incorporated herein by reference in its entirety.

BACKGROUND OF THE INVENTION

1. Field of the Invention

The present invention is related to a method for enhancing the secretion of GLP-1 of the intestinal endocrine cell using bitter compound.

2. The Prior Arts

Glucagon-like peptide, GLP-1, a member of glucagon peptide family having 30 or 31 amino acids, is a known type of incretin which is secreted from intestinal endocrine L-cells. As a nerve reflex mechanism, GLP-1 is secreted within minutes after the food intake as well as when the food directly contact the intestinal endocrine L-cells. The functions of GLP-1 are as follow: enhancing the secretion of glucose-dependent insulin of pancreatic beta cells, increasing insulin sensitivity, suppressing the secretion of glucagon, suppressing appetite, lowering gastric emptying rate, and enhancing the growth, differentiation and regeneration of pancreatic beta cells as well as preventing them from apoptosis. When L-cells are stimulated, membrane depolarization and the increase of intracellular cAMP or $Ca^{2+}$ concentration promotes intracellular secretary vesicles to fuse with cellular membrane, thus, resulting in the release of GLP-1. However, once GLP-1 is secreted from L-cells, it is soon degraded by dipeptidyl peptidase 4, DPP-4, which is extensively distributed in blood plasma, epidermal cells or the surface of endothelial cells. Only 10-15% of the secreted GLP-1 can enter the systemic circulation in its active form and its half-life in the systemic circulation is approximately 2 minutes.

Triterpenoids are metabolites of isopentenyl pyrophosphateoligomers consist of 30 carbon atoms and are mostly formed by the linkage of 6 isoprene units. According to estimation, there are more than 2,000 types of triperpenoid naturally existed in animals or plants. Triperpenoid in plants are mostly in the form of free, glycosides, or ester, and are mainly tetracyclic or pentacyclic triperpenoid compounds. There are many known pharmaceutical and pharmacological effects of triperpenoid compounds, such as: anti-inflammation, analgesia, cardiotonic, sedative, anti-oxidation, anti-virus, anti-bacterial, anti-allergic, antipruritic, antiangiogensis and muscle relaxation.

As mentioned above, the physiological phenomenon of intestinal endocrine L-cells detecting certain food or nutrients and resulting in the secretion of insulin to decrease blood glucose level via hormone stimulation is called incretin effect. Intestinal endocrine L-cell is located in intestine tract and the different taste receptors on its membrane are directly exposed to nutrients or substances in the intestine tract enhancing the secretion of metabolic hormone.

In light of the ability of adjusting blood glucose level and the limitation of reaction time and activity of incretin, as well as the feasibility of stimulating taste receptors on the intestinal endocrine L-cells located in the intestine tract to cause incretin effect as described above, it is necessary to provide a medicament or healthy victual which is able to regulate the secretion of GLP-1 of the intestinal endocrine L-cells upon discovering specific receptor-ligand interactions.

SUMMARY OF THE INVENTION

As a result, the present invention provides a method for enhancing the secretion of GLP-1 of the intestinal endocrine L-cell using a bitter compound, wherein the bitter compound is a cucurbitane-triterpenoid or allyl isothiocyanate and the intestinal endocrine cell is STC-1.

One aspect of the present invention is to provide a cucurbitane-triterpenoid compound of formula I:

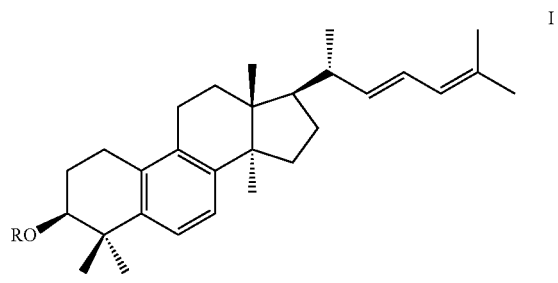

wherein R is selected from hydrogen group, alkyl group, acyl group, a chain of glucose $(glucose)_n$, and a chain of allose $(allose)_n$; n is 0 or any integral number from 1 to 7 upon R being a chain of glucose or a chain of allose. Preferably, when R is hydrogen group, the compound is represented as formula II:

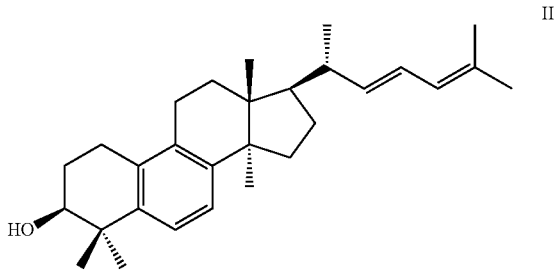

which is known as 19-nor-cucurbita-5(10),6,8,22(E),24-pentaen-3β-ol.

Another aspect of the present invention is to provide a cucurbitane-triterpenoid compound of formula III:

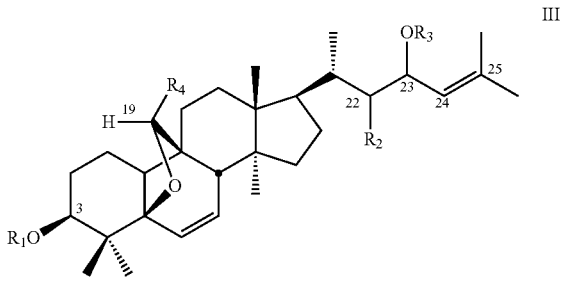

wherein $R_1$ is hydrogen group, a chain of glucose or a chain of allose; $R_2$ is hydrogen group, hydroxyl group, a chain of oxygenated glucose $O(glucose)_n$, or a chain of oxygenated allose $O(allose)_n$. When $R_1$, $R_2$, and $R_3$ are all hydrogen, the compound is represented as formula IV:

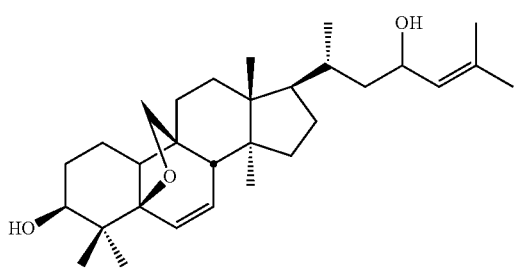

which is known as 5β,19-epoxycucurbita-6,24-diene-3β, 23ξ-diol.

In another aspect of the present invention, the bitter compound is, preferably, from *Momordica charantia*.

Another aspect of the present invention, the method as previously mentioned is the influence upon secretion of GLP-1 of the intestinal endocrine cell line STC-1 when allyl isothiocyanate and bitter taste receptor inhibitor or PLC inhibitor are co-administered; the bitter taste receptor herein is TAS2R38.

Another aspect of the present invention is to provide a pharmaceutical composition for enhancing the secretion of GLP-1 of the intestinal endocrine cell, which comprises of a pharmaceutically acceptable carrier and an effective amount of the bitter compound, wherein the bitter compound is a cucurbitane-triterpenoid or allyl isothiocyanate.

According to the method for enhancing the secretion of GLP-1 of the intestinal endocrine L-cell using a bitter compound of the present invention, the secretion of GLP-1 can be effectively increased, hence, it is reliable for the development of medicament or healthy victual.

The present invention is further explained in the following embodiment illustration and examples. Those examples below should not, however, be considered to limit the scope of the invention, it is contemplated that modifications will readily occur to those skilled in the art, which modifications will be within the spirit of the invention and scope of the appended claims.

DETAILED DESCRIPTION OF THE PREFERRED EMBODIMENT

Definition

Figure 1:
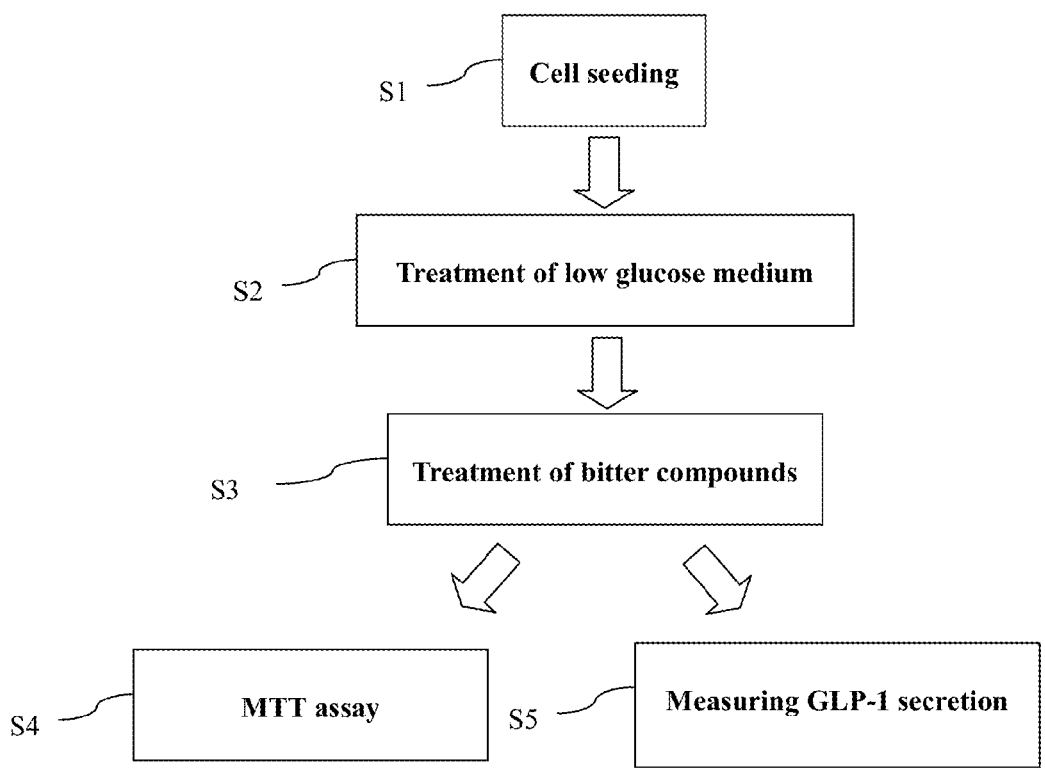
FIG. 1, flow chart for the experiment of bitter compound stimulating the secretion of GLP-1.

As used herein, the term "composition" refers to any types of compound or composition including powder, mixture of powder and its similar form, emulsion, suspension, and solution.

In one embodiment, R is a carbon-carbon single bond and n is 0 or any integral number from 1 to 7, more preferably 0 or any integral number from 1 to 5, most preferably 0 or any integral number from 1 to 3.

The embodiment of the present invention use a proglucagon-expression cell line STC-1 for study. The STC-1 cells are divided into the experimental groups and the control group. The control groups are also called vehicle groups, which is the comparison of result of each experiment taken as 1. The secretion of GLP-1 is obtained by calculating the data gathered from the experiment using the standard curve after treating intestinal endocrine cell line STC-1 with different bitter compounds. Cell viability is measured by MTT assay after treating intestinal endocrine cell line STC-1 with different bitter compounds. The ratio of the amount of GLP-1 secreted to the cell viability in each experiment is the fold of that given bitter compound stimulating the secretion of GLP-1 of the intestinal endocrine cell line STC-1. By comparing experimental groups and vehicle groups, the difference between different bitter compounds in terms of their ability to stimulate the secretion of GLP-1 of the intestinal endocrine cell line STC-1 can be observed. Moreover, co-administering specific bitter compound, bitter taste receptor inhibitor or phospholipase C (PLC) inhibitor can further determine the bitter taste receptor corresponded to the bitter compound. The above mentioned testing methods are explained in detailed as follow:

Materials and Methods

Flow Chart and Steps for the Experiment of Bitter Compound Stimulating the Secretion of GLP-1

The intestinal endocrine cell line STC-1 used in the present invention (ATCC number: SD-5482) is provided by Dr. Hanahan (Department of Biochemistry & Biophysics, University of California, San Francisco, USA) and is a proglucagon-expression cell line from cancerous intestinal endocrine cell of double transgenic mouse (Rindi et al., 1900). STC-1 is an adherent cell which is able to secrete various types of hormone including glucagon, somatostatin, amlyin, secretin, and, more significantly, cholecystokinin (CCK) and glucagon-like peptide-1 (GLP-1).

For bitter compounds, the present invention regards the compound of formula I and III in the embodiments.

Multiple side-chain structures consist of monosaccharide introduced by N. X. Nhiem, et al. can be seen as a reference, wherein the side-chain structure, particularly the C-3 side-chain, is, more preferably, a pharmacologically acceptable monosaccharide, and, more preferably allose or glucose (N. X. Nhiem, et al. Magn. Reson. Chem. 2010, 48, 392-396).

Multiple side-chain structures consist of monosaccharide is also introduced by T. Murakami, et al. and can be seen as a reference, wherein the side chains are more preferably pharmacologically acceptable subtituents and are, more preferably, selected from hydrogen group, hydroxyl group, alkyl group, alkoxy group, chain of allose, chain of oxygenated allose, chain of glucose, or chain of oxygenated glucose (T. Murakami, et al. Chem. Pharm. Bull. 49(1) 54-63 (2001)).

For the embodiment of the ability of bitter compound stimulating secretion of GLP-1 of the intestinal endocrine cell line STC-1, the experiment procedure of the stimulation of GLP-1 secretion is referred in FIG. 1.

Each step of FIG. 1 is explained as follow:

S1: $6.39 \times 10^4$ cells were planted with 10% FBS DMEM (high glucose) in 48-well culture tray and were incubated for 48 hours.

S2: After 48 hours when the cell growth reached 85%, culture medium was changed into 10% FBS DMEM (low glucose) for a 3-hour starvation and then followed by the treatment of 0.2% BSA DEME (low glucose).

S3: The STC-1 cell line was treated by a bitter compound.

S4: Supernatant was collected via centrifugation and the remaining growth medium was removed after 1 hour and the amount of cell was measured by MTT assay.

S5: Supernatant from S4 was centrifuged again at 500×g for 5 minutes. After eliminating cell debris, the resulting supernatant was collected and stored at −80° C. for the analysis of GLP-1 secretion using commercial kit Millipore EGLP-35K. The sensitivity of the kit is between 2-100 pM. The amount of GLP-1 secreted of each vehicle group is between 50-150 pM according to the batch, therefore, it is advised that the supernatant being diluted 4 times before the analysis. The result was shown in the amount of GLP-1 secreted per unit cell. To prevent over-discrepant results between batches and for the ease of statistic, each vehicle group was taken as 1, which is the comparison of result of each sample of that experiment.

Measuring the Amount of GLP-1 Secreted

Before measuring the amount of GLP-1 secreted, all reagents were placed on ice until fully dissolved. 10× washing buffer concentrate were diluted 10 times using distilled water; STC-1 cell line was dissolved using 1 mL distilled water and was diluted 200 times using phosphate buffered saline (PBS). 300 μL/well of 1× wash buffer were added and were placed for 5 minutes at room temperature then were poured out. 200 μL/well of assay buffer were added to NSB, while 100 μL/well of assay buffer were added to the remaining wells. 100 μL of Standards, QC or STC-1 cell line were then added to the wells accordingly, and then the 96-well plate was shaken moderately for an even mixture within each well. Plates were then being sealed allowing reaction to take place at 4° C. for 20-24 hours. Plates were then washed 5 times by 300 μL/well of 1× wash buffer and placed for 5 minutes. 200 μL/well of detection conjugate was added allowing reactions to take place at room temperature for 2 hours. It was then washed 3 times by 300 μL/well of 1× wash buffer. 200 μL/well of diluted STC-1 cell line was added allowing reaction to take place at room temperature and light-free environment for approximately 20 minutes. 50 μL/well of stop solution was added to stop the reaction at room temperature and light-free environment for 5 minutes. Finally, the concentration of GLP-1 was calculated using the data obtained and the standard curve.

MTT Assay

Principle of MTT assay: Methylthiazolyldiphenyl-tetrazolium bromide (MTT), or 3-(4,5-cimethylthiazol-2-yl)-2,5-diphenyl tetrazolium bromide, is a yellow dye which can be reduced by dehydrogenase of mitochondria in living cells, forming an insoluble purple crystal, formazan. Thus, it is often used for the screening of the effect of materials upon the cell growth and proliferation. As a result, measuring the absorbance at 540 nm after dissolving the purple crystals with solvent and calculating with the known standard curve of cell number, the relative cell viability can be obtained. In the experiment, Dulbecco's Modified Eagle Medium, DMEM, was used to dilute stock MTT solution (5 mg/mL) 10 times into 0.5 mg/mL MTT solution for further usage. After collecting the supernatant containing GLP-1 and removing the remaining medium, 110 μL of MTT solution were added to each well of the 48-well culture tray and were incubated at 37° C. in 5% $CO_2$ incubator for 3 hours. Then, 200 μL of HCl isopropanol were added to crystallize the crystals. Finally, the absorbance at 540 nm was measured and the cell viability can be calculated through comparison with the vehicle groups.

Data of the present invention were presented as means±SD and were analyzed using SAS9.0 statistical program. Differences between the Student's t test and vehicle groups were selected and the difference between batches was eliminated by Randomized Complete Block Design, BCBD. * indicates that there were significant difference, *P<0.05, P<0.01, and *P<0.001 were considered significant.

Example 1

Ability of Allyl Isothiocyanate Stimulates the Secretion of GLP-1 of the Intestinal Endocrine Cell Line STC-1

Allyl isothiocyanate (purchased from Sigma-Aldrich Co., ID: 36682) was dissolved in 70% ethanol and was prepared into 0.5M stock solution. The solution was distributed into small vials and was stored in refrigerator at −20° C.

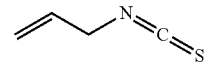

Cells treated by 1.0 μM, 2.0 μM, 5.0 μM, and 10.0 μM of allyl isothiocyanate solution can all significantly increase the secretion of GLP-1 comparing to the vehicle groups at a dose-dependent manner. The result of STC-1 cell line treated by 10.0 μM allyl isothiocyanate was the most significant, which is 4.06 fold of vehicle group. Results are presented in FIG. 1.

Example 2

Comparison of the Abilities of Allyl Isothiocyanate and Other Bitter Compounds Stimulate the Secretion of GLP-1 of the Intestinal Endocrine Cell Line STC-1

Cells were also treated by other bitter compounds at different concentrations, such as: Caffeine at 0.1 mM, 0.5 mM, and 1.0 mM; Denatonium benzoate at 1.0 mM, 2.5 mM, and 5.0 mM; Acesulfame K at 1.0 mM, 5.0 mM, and 10.0 mM; Saccharin at 0.3 mM, 0.5 mM, and 1.0 mM; Brucine at 1.0 μM, 5.0 μM, 10.0 μM, 50.0 μM and 200.0 μM; Chloroquine at 0.5 μm, 1.0 μM, 2.5 μM, 5.0 μM, and 10.0 μM; Strychnine at 0.1 μM, 5.0 μM, 10.0 μM, 50.0 μM, and 100.0 μM; Limonin at 20 μM, 50 μM, 100 μM, and 200 μM; Quinine at 5.0 μM, 25.0 μM, 50.0 μM, and 80.0 μM. As shown in Table 1, allyl isothiocyanate exhibit the best level of activity.

TABLE 1

The largest fold and concentration of each bitter compound stimulate the secretion of GLP-1 of the intestinal endocrine cell line STC-1

| Bitter compound | Concentration | Fold |
| --- | --- | --- |
| Caffeine | 1 mM | ↑1.72 |
| Denatonium benzoate | 2.5 mM | ↑2.97 |
| Acesulfame K | 10 mM | ↑1.90 |
| Saccharin | 1 mM | ↑4.84 |
| Brucine | 50 μM | ↑1.54 |
| Chloroquine | 5 μM | ↑1.78 |
| Strychnine | 50 μM | ↑1.91 |
| Limonin | 200 μM | ↑1.22 |
| Quinine | 80 μM | ↑1.90 |
| Allyl isothiocyanate | 10 μM | ↑4.06 |

Example 3

Influence Upon Secretion of GLP-1 of the Intestinal Endocrine Cell Line STC-1 when Allyl Isothiocyanate and Bitter Taste Receptor Inhibitor or PLC Inhibitor are Co-Administered Allyl isothiocyanate and probenecid, a bitter taste receptor inhibitor, or U73127, a PLC inhibitor, are co-administered.

Figure 2:
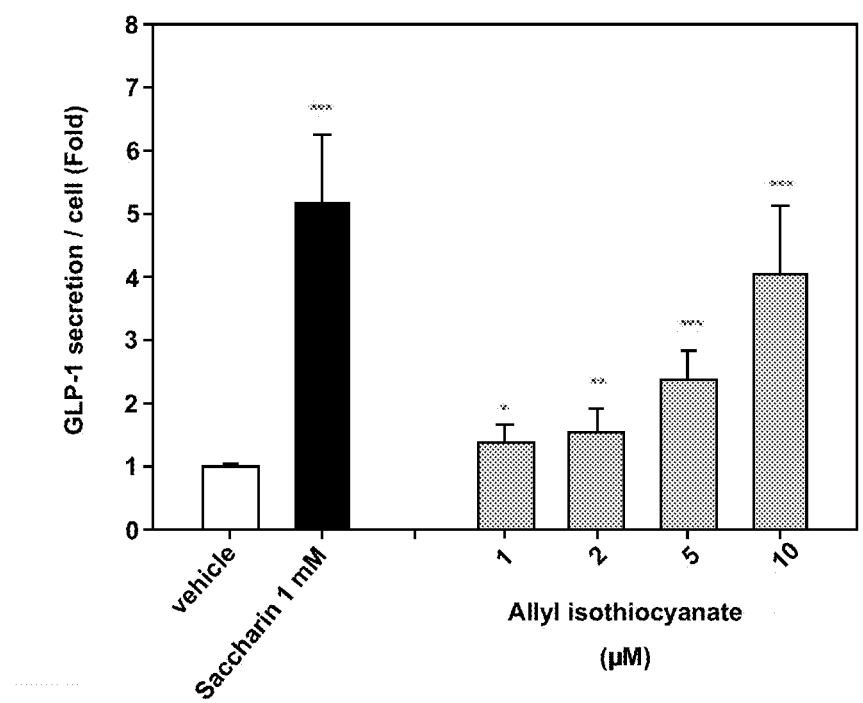
FIG. 2, the ability of allyl isothiocyanate stimulates the secretion of GLP-1 of the intestinal endocrine cell line STC-1.

The secretion of GLP-1 of the intestinal endocrine cell line STC-1 was significantly increased when allyl isothiocyanate was solely applied, which are 1.44, 2.05 and 3.44 fold of the vehicle group (p<0.05), respectively. However, when 0.5 mM of probenecid was jointly applied, the results decrease to 1.14, 1.40 and 1.93 fold of the vehicle group (p<0.001), respectively; when 1.0 mM of probenecid was jointly applied, the results further decrease to 0.86, 1.07 and 1.51 fold of the vehicle group (p<0.001), respectively. Results are presented in FIG. 2.

Allyl isothiocyanate, an agonist specific to TAS2R38, can stimulate the secretion of GLP-1. The secretion of GLP-1 of the intestinal endocrine cell line STC-1 is significantly lower when co-administering probenecid than when solely administering allyl isothiocyanate. Thus, allyl isothiocyanate can stimulate the secretion of GLP-1 of the intestinal endocrine cell line STC-1 through TAS2R38.

Example 4

Ability of Compound of Formula II Stimulates the Secretion of GLP-1 of the Intestinal Endocrine Cell Line STC-1

Compound of formula II is 19-nor-cucurbita-5(10),6,8,22 (E),24-pentaen-3β-ol:

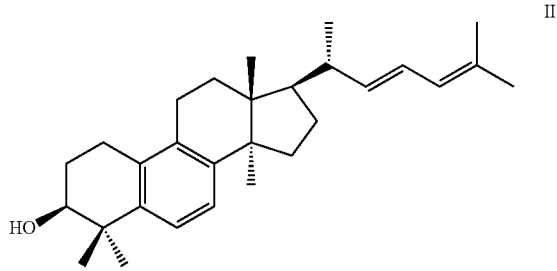

To obtain compound of formula II, freeze dry powder of *Momordica charantia* was extracted by ethyl acetate and the extract was further prepared as a non-saponifiable fraction without fatty acid by base hydrolysis. The non-saponifiable fraction was purified and isolated using GC-MS and HPLC. The extracted powder of *Momordica charantia* was then being extracted again using ethanol. This ethanol extract was then underwent acid hydrolysis followed by purification and isolation. Detailed of the above procedure can be referred to US20120252772.

Figure 3:
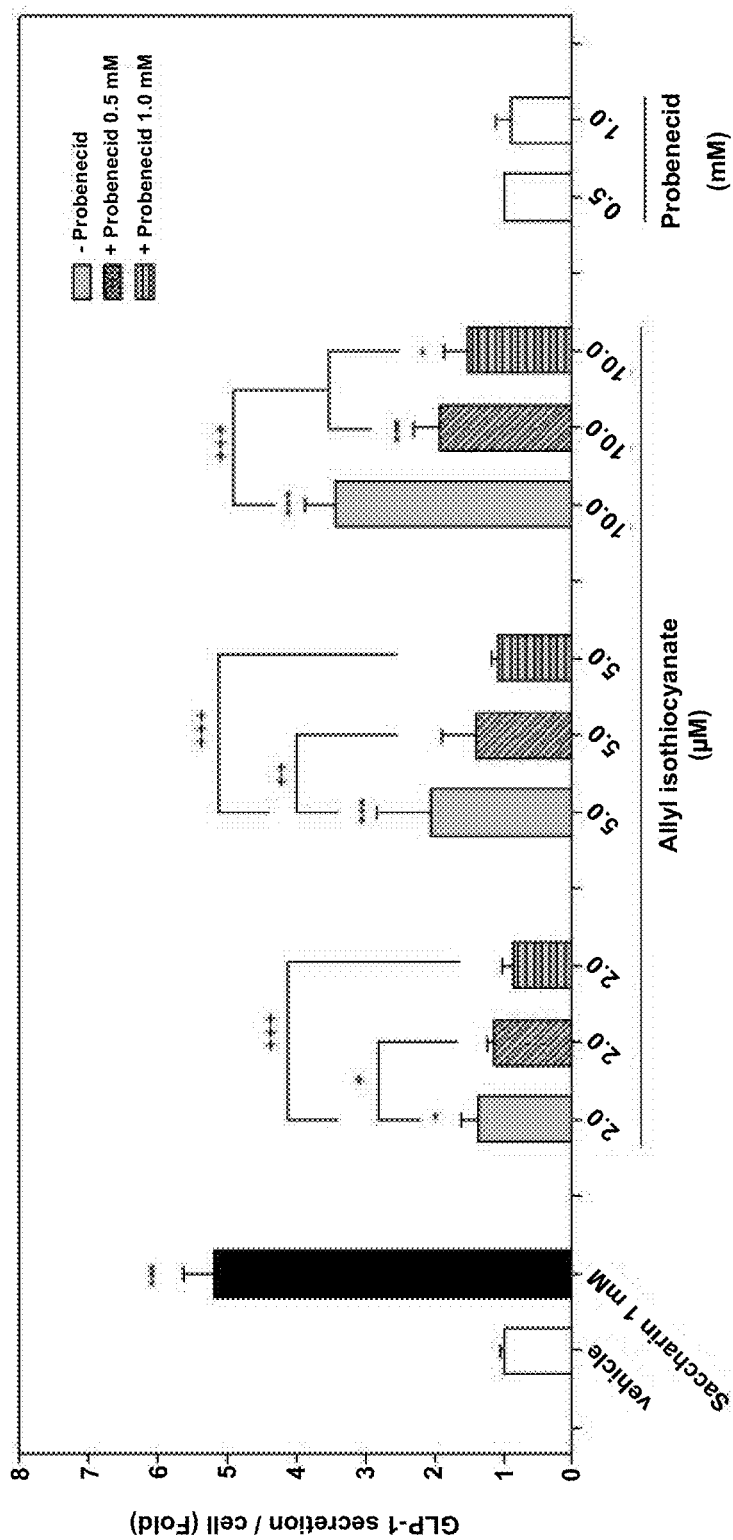
FIG. 3, the influence upon secretion of GLP-1 of the intestinal endocrine cell line STC-1 when allyl isothiocyanate and bitter taste receptor inhibitor or PLC inhibitor are co-administered.

According to the maximum dosage acceptable by the cells, concentrations being tested were gradually decreased. Compound of formula II significantly increase the secretion of GLP-1 by 1.66, 2.28, 4.53, 6.05, and 6.16 fold comparing to the vehicle group when cells were treated by 5, 20, 50, 100, and 200 μg/mL (FIG. 3, p<0.05).

As a result, triterpenoids having moderate or low polarity with shorter or carbohydrate-free bases in *Momordica charantia* exhibit better ability regarding stimulation of GLP-1 secretion.

Example 5

Ability of Compound of Formula IV Stimulates the Secretion of GLP-1 of the Intestinal Endocrine Cell Line STC-1

Compound of formula IV is 513,19-epoxycucurbita-6,24-diene-313,234-diol:

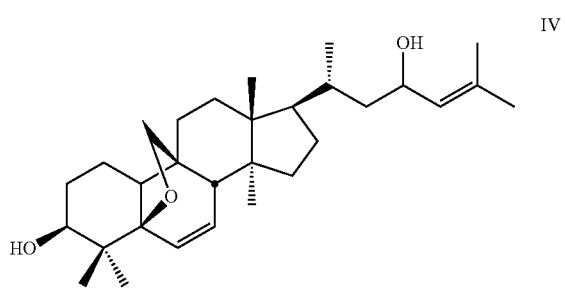

To obtain compound of formula IV, freeze dry powder of *Momordica charantia* was extracted by ethyl acetate. After base hydrolysis, both non-saponifiable and saponifiable fractions were found. The non-saponifiable fraction was then purified and isolated using HPLC. Detailed of the above procedure can be referred to US20120252772.

Figure 4:
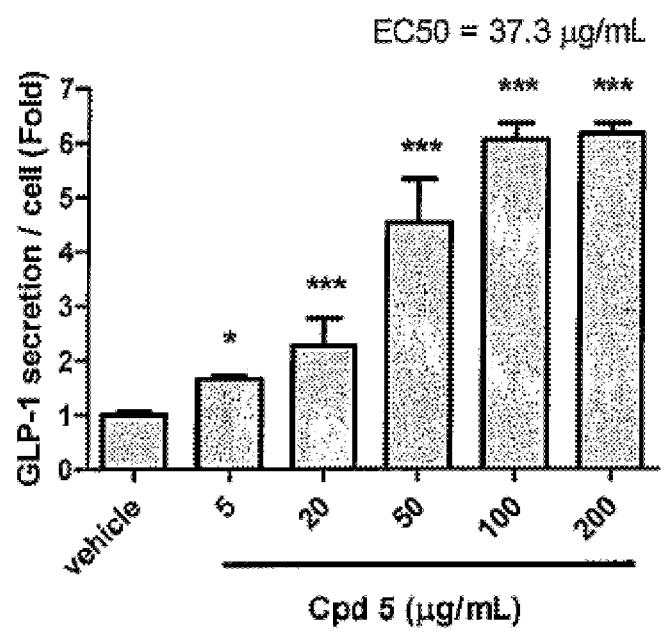
FIG. 4, the ability of compound of formula II stimulates the secretion of GLP-1 of the intestinal endocrine cell line STC-1.
Figure 5:
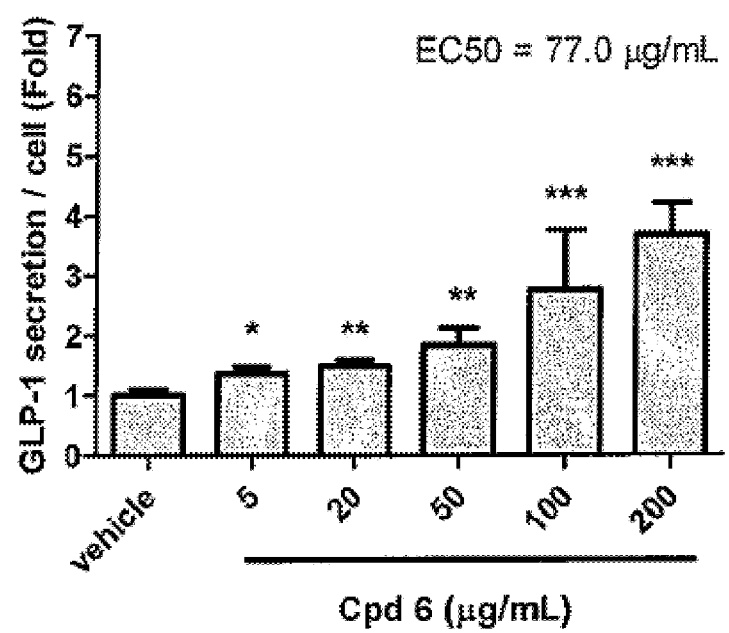
FIG. 5, the ability of compound of formula IV stimulates the secretion of GLP-1 of the intestinal endocrine cell line STC-1.

According to the maximum dosage acceptable by the cells, concentrations being tested were gradually decreased. Compound of formula IV significantly increase the secretion of GLP-1 by 1.37, 1.49, 1.84, 2.76, and 3.68 fold comparing to the vehicle group when cells were treated by 5, 20, 50, 100, and 200 μg/Ml (FIG. 4, p<0.05).

As a result, triterpenoids having moderate or low polarity with shorter or carbohydrate-free bases in *Momordica charantia* exhibit better ability regarding stimulation of GLP-1 secretion.

Furthermore, the above cucurbitane-triterpenoid or allyl isothiocyanate can be used as a pharmaceutical composition for enhancing the secretion of GLP-1 of the intestinal endocrine cell, which comprises compounds of formula I-IV or allyl isothiocyanate, the combination thereof or the pharmaceutically acceptable salt thereof, and a diluent, excipient, or carrier.

The above active ingredient, whether in the form of single compound of a pharmaceutical composition, is potentially reliable for the development of medicament as treatment for symptoms caused by insufficient or deficient GLP-1 secretion. Meanwhile, cucurbitane-triterpenoid compound of formula I-IV can also combine with certain drugs for hypoglycemia, thus is potentially reliable for the development of healthy victual as treatment for symptoms caused by insufficient or deficient GLP-1 secretion.

The compound or pharmaceutical composition for enhancing the secretion of GLP-1 of the intestinal endocrine cell provided in present invention is applicable and valuable to the industry. Those embodiments above are better results, and should not, however, be considered to limit the scope of the invention, it is contemplated that modifications will readily occur to those skilled in the art, which modifications will be within the spirit of the invention and scope of the appended claims.

What is claimed is:

1. A method for enhancing GLP-1 secretion of an intestinal endocrine cell, comprising administering to the intestinal endocrine cell an effective amount of a bitter compound, wherein the bitter compound stimulates a bitter taste receptor TAS2R38 on the intestinal endocrine cell to enhance GLP-1 secretion by the intestinal endocrine cell, and wherein the bitter compound is allyl isothiocyanate at a concentration of at least 1 µM.

2. The method according to claim 1, wherein the intestinal endocrine cell is proglucagon-expression cell line STC-1.

* * * * *